United States Patent [19]

Borchard

[11] Patent Number: Plant 5,750

[45] Date of Patent: Jun. 17, 1986

[54] BORCHARD AVOCADO TREE

[76] Inventor: Edward C. Borchard, 701 E. Gonzales Rd., Oxnard, Calif. 93030

[21] Appl. No.: 583,346

[22] Filed: Feb. 24, 1984

[51] Int. Cl.[4] ..... A01H 5/03

[52] U.S. Cl. ..... Plt./44

[58] Field of Search ..... Plt./44

*Primary Examiner*—Robert E. Bagwill

*Attorney, Agent, or Firm*—John E. Kelly

[57] ABSTRACT

The new avocado tree is characterized by its relatively greater usefulness compared to the Topa Topa as a root stock and in prevention of chlorosis in soil conditions where trees are prone to become chlorotic.

3 Drawing Figures

This invention relates to a new and distinct variety of avocado tree and is characterized as to primary novelty by its usefulness as a root stock and in prevention of chlorosis in soil conditions where trees are prone to become chlorotic.

The novel avocado tree was discovered on the Ed Borchard Ranch in Oxnard, Ventura County, Calif. I have named this new tree the Borchard Avocado Tree. The tree may be reproduced by grafting a stick of it onto any root stock. The tree in most instances will be propagated as a clonal root stock, utilizing the clonal methods set forth in U.S. Pat. No. 4,012,866 issued Mar. 22, 1977. The asexual reproduction of the instant variety of avocado tree by grafting has resulted in the provision of an extremely useful root stock capable of preventing chlorosis in soil conditions where trees are prone to become chlorotic. Observations of the new tree may be made at the Ed Borchard Ranch, 701 E. Gonzales Road, Oxnard, Calif.

In FIG. 1 of the accompanying drawings, there is shown at the top two of the new and distinct varieties of avocado for comparison with two conventional Topa Topa avocados shown immediately therebeneath in the middle row and two conventional Fuerte avocados shown in the bottom row. The skin of the new avocado is black and thin, typically Mexican. The fruit itself is slightly elongate but is not necky, the same being blunter than the Topa Topa and thicker necked than the Fuerte.

FIG. 2 of the accompanying drawings shows the new avocado on top split in half for comparison with a conventional Topa Topa shown below in the middle row also cut in half and a conventional Fuerte in the bottom row, cut in half. It can be seen that the seed size is about average, that is, corresponds substantially in size to the seed of the Topa Topa and Fuerte.

FIG. 3 illustrates a typical cluster of the new and distinct variety of avocado of this invention and also illustrates the foliage or leaves.

Following is an outline description in greater detail of the distinct variety of the avocado tree of this invention:

PLANT

Form: Normal spreading.

Growth: Vigorous.

Wood: New wood is green and smooth; mature wood is brown and rough.

Foliage: Single leaf.

*Size.*—Normal.

Quantity: Abundant.

*Color.*—Dark green on upper surface, medium green on lower surface.

*Shape.*—Elongated oval — pointed.

Texture: Upper surface is leathery and minutely pebbled. There are pronounced veins on the lower surface.

*Edge.*—The leaf edge is somewhat wavy with a smooth outline.

Leaf stem color: The leaf petiole is yellow with dark green lateral flecks.

Fruit: The skin is black and thin and typically Mexican. The fruit does not cluster excessively. The tree bears well annually. The flesh is firm when first picked and then soft when ripe. It is not stringy and is moderately oily.

*Form.*—Slightly elongate without being necky. The fruit is blunter than the Topa Topa and thicker necked than the Fuerte.

*Aspect.*—Smooth.

Color at maturity: Black.

Size at maturity: Length and width about the same as the Topa Topa.

*Seed.*—The seed size is normal, corresponding to that of the Fuerte.

Blooming habit: Blooming period is from February to April.

Bearing habit: September to November.

As stated heretofore, the most distinguishing characteristic of this new and distinct variety of avocado tree is its usefulness as a root stock and its prevention of chlorosis in soil conditions where trees are prone to become chlorotic.

The state law of California requires that avocados contain eight percent (8%) oil. The oil content of small, medium and large avocados of the present invention is well in excess of this eight percent.

The avocado tree and its fruit as described herein may vary in slight detail due to climate and soil conditions under which the variety is grown.

What is claimed is:

1. A new and distinct variety of avocado substantially as shown and described, characterized particularly by its usefulness as a root stock and in prevention of chlorosis in soil conditions where trees are prone to become chlorotic.

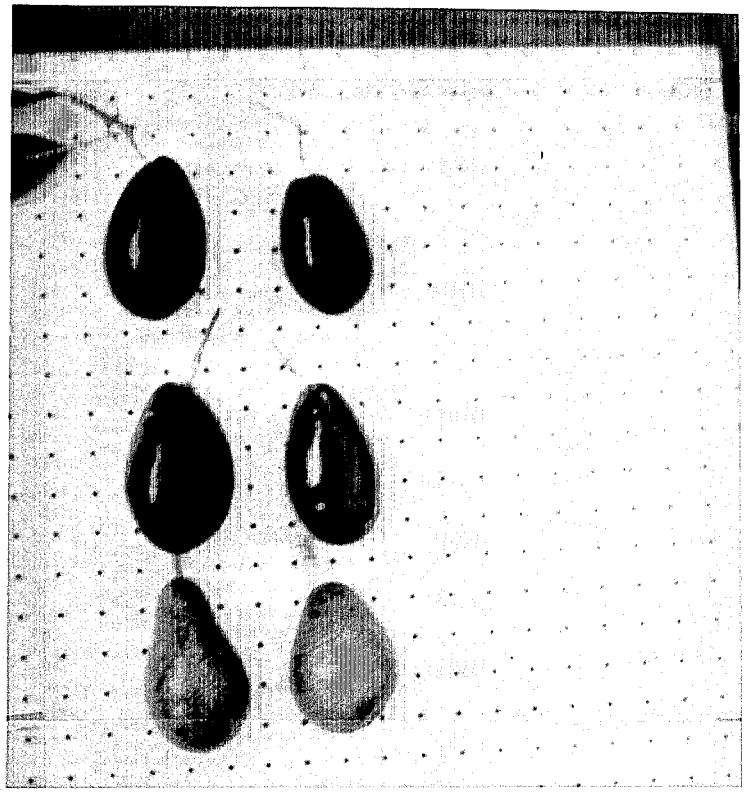
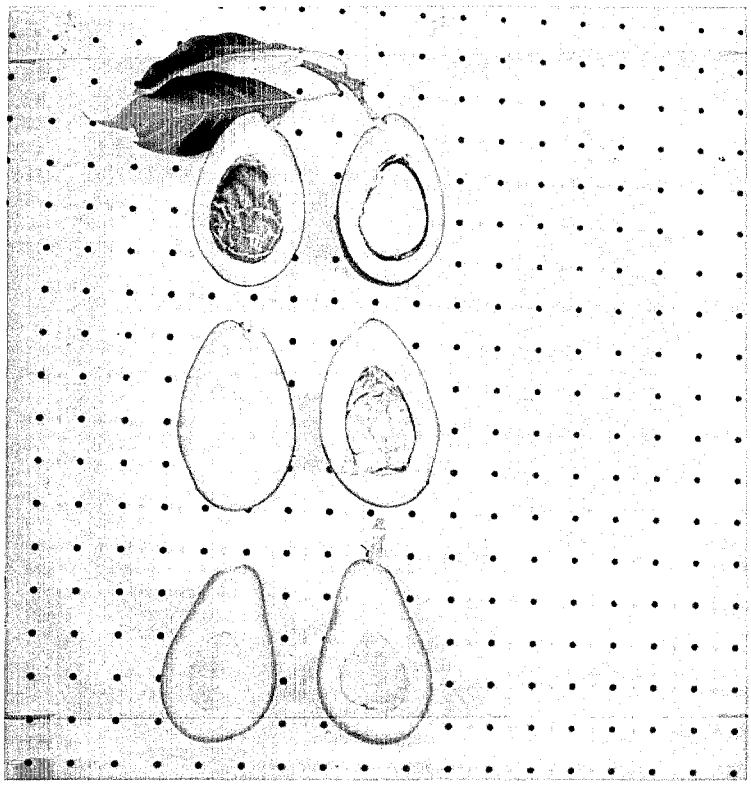

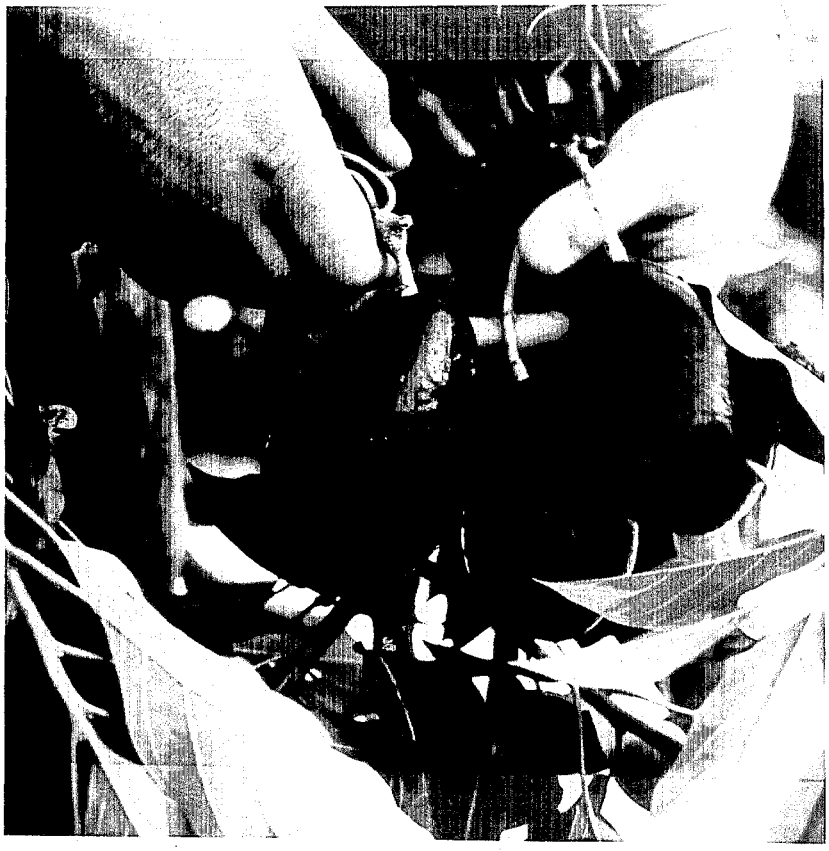

* * * * *